United States Patent [19]

Brown, III et al.

[11] Patent Number: 4,916,056
[45] Date of Patent: Apr. 10, 1990

[54] SOLID-PHASE ANALYTICAL DEVICE AND METHOD FOR USING SAME

[75] Inventors: William E. Brown, III, Grayslake; Sarah E. Safford, Libertyville; John M. Clemens, Gurnee, all of Ill.

[73] Assignee: Abbott Laboratories, Abbott Park, Ill.

[21] Appl. No.: 173,979

[22] Filed: Mar. 28, 1988

Related U.S. Application Data

[63] Continuation-in-part of Ser. No. 831,013, Feb. 18, 1986, which is a continuation-in-part of Ser. No. 784,416, Oct. 4, 1985, abandoned.

[51] Int. Cl.[4] ............... G01N 33/53; G01N 33/543; G01N 33/545; C12M 1/12
[52] U.S. Cl. .................. 435/7; 435/805; 435/810; 435/311; 436/518; 436/531; 436/535; 436/807; 436/808; 422/56; 422/57; 422/101; 210/238
[58] Field of Search ............ 435/7, 34, 36, 288, 435/805, 810, 5, 6, 311; 436/807, 808, 809, 518, 527, 528, 530, 531, 535, 169, 170, 161, 162, 818; 422/55, 56, 57, 58, 59, 60, 61, 101, 68, 70; 210/238

[56] References Cited

U.S. PATENT DOCUMENTS

| | | | |
|---|---|---|---|
| 3,260,413 | 7/1966 | Natelson | 422/66 |
| 4,059,407 | 11/1977 | Hochstrasser . | |
| 4,099,886 | 7/1978 | Oliveira | 422/56 X |
| 4,219,335 | 8/1980 | Ebersole | 436/808 X |
| 4,340,564 | 7/1982 | Harte et al. | 422/56 |
| 4,366,241 | 12/1982 | Tom et al. | 435/5 X |
| 4,472,353 | 9/1984 | Moore | 422/58 |
| 4,477,575 | 10/1984 | Vogel et al. | 436/170 |
| 4,496,654 | 1/1985 | Katz et al. | 435/7 |
| 4,533,629 | 8/1985 | Litman et al. | 435/7 |
| 4,540,659 | 9/1985 | Litman et al. | 435/7 |
| 4,541,987 | 9/1985 | Gundagno | 422/56 |
| 4,558,013 | 12/1985 | Marinkovich et al. | 436/513 |
| 4,632,901 | 12/1986 | Valkirs et al. | 435/5 |
| 4,649,121 | 3/1987 | Ismail et al. | 436/14 |
| 4,740,468 | 4/1988 | Weng et al. | 435/7 |
| 4,748,042 | 5/1988 | Linnecke et al. | 422/56 X |

FOREIGN PATENT DOCUMENTS

0200381 11/1986 European Pat. Off. .

*Primary Examiner*—Randall E. Deck
*Attorney, Agent, or Firm*—Thomas D. Brainard

[57] ABSTRACT

A novel material and device useful in solid-phase binding assays to determine the presence or amount of an analyte in a test sample, particularly antigens, antibodies, or other ligands or DNA segments. The material and device comprises a reaction site having procedural controls and an analyte binding area capable of being simultaneously contacted by the sample and reagent used in the performance of the assay. The procedural controls and analyte binding areas operate to provide readable results as to the presence or absence of analyte and simultaneously verify the assay procedure and therefore the assay result.

4 Claims, 4 Drawing Sheets

SOLID-PHASE ANALYTICAL DEVICE AND METHOD FOR USING SAME

BACKGROUND OF THE INVENTION

This application is a continuation in part of U.S. Patent Application Ser. No. 831,013, filed Feb. 18, 1986, which is a continuation in part of U.S. Patent Application Ser. No. 784,416 filed Oct. 4, 1985, now abandoned.

TECHNICAL FIELD

This invention relates generally to analytical devices having a plurality of readable results through the use of procedural control and analyte binding areas on a single reaction site. More particularly, the present invention relates to novel devices useful in the performance of binding assays, and to improved analytical devices. The concepts of the present invention are especially advantageous in the performance of enzyme immunoassay of biological fluids and products such as serum, plasma, whole blood, urine, spinal and amniotic fluids, mucus and the like.

BACKGROUND ART

Various analytical procedures and devices are commonly employed in assays to determine the presence and/or concentration of substances of interest or clinical significance which may be present in fluids or other materials. Such clinically significant or interesting substances are commonly termed "analytes", and can include, for example, antibodies, antigens and the broad category of substances commonly known by the term "ligands". Particularly with respect to the diagnosis and treatment of disease or other conditions of the human body, the accurate determination, on a timely basis, of the presence or amount in biological fluids of certain analytes which are of clinical significance can have a profound influence on the ability of health care professionals to treat and manage pathological physical disorders, or to make an early and accurate determination of physiological conditions such as pregnancy.

One assay methodology which has been increasingly applied in the diagnosis of various disorders and conditions of the human body is the binding assay, and in particular the type of binding assay known as enzyme immunoassay (EIA). EIA techniques take advantage of the mechanisms of the immune systems of higher organisms, wherein antibodies are produced in response to the presence of substances (i.e., antigens) in the organisms which are pathogenic or foreign to the organisms. One or more antibodies are produced in response to and are capable of reacting with a particular antigen, thereby creating a highly specific reaction mechanism which can be advantageously utilized, in vitro, to determine that particular antigen.

Conventional EIA procedures involve a series of wet chemistry steps using liquid reagents, wherein an analyte in a sample biological fluid under assay, e.g., an antigen or antibody in a test sample of urine, whole blood or serum, is detected. In one type of EIA procedure, the analyte in the sample initially becomes bound to a corresponding antigen or antibody reagent which is introduced into the sample. Then, another antigen or antibody is introduced. This second antigen or antibody, however, is one which has been labeled or conjugated with an enzyme or other substance capable of producing or causing, often when reacted with or in the presence of an additional, suitable indicator reagent such as a chromogen or dye, a detectable response such as color development. The detectable response so produced can then be read and interpreted, visually or instrumentally, as an indication or measure of the presence or amount of the antigen or antibody present in the original sample.

Solid-phase EIA procedures are generally considered preferable for both antibody and antigen assays because of their safety, ease of use, specificity and sensitivity by comparison with heretofore-employed liquid reagent binding assay techniques such as radioimmunoassay (RIA), and other conventional wet chemistry methodologies. Moreover, the possibility of reading color development instrumentally, such as by use of a spectrophotometer, is a feature of many solid-phase EIA techniques which has resulted in their wide spread use.

Thus, in one type of conventional solid phase EIA "sandwich" assay, a test sample suspected of containing an antibody or antigen of interest is initially contacted by a solid, substantially inert plastic or glass bead or other support material which has been previously coated with a protein or another substance capable of reaction with the antigen or antibody to retain it on the surface of the support, either by immobilization of the antigen or antibody on the surface or by chemical binding therewith. A second antigen or antibody, which is usually conjugated (linked chemically) with an enzyme, is then added and this second species becomes bound to its corresponding antibody or antigen on the support. Following one or more washing step(s) to remove unbound material, an indicator substance, for example, a chromogenic substance reactive in the presence of the enzyme, is then added and, because of its sensitivity to the presence of the enzyme, produces a detectable color response. The development of the color response, its intensity, etc. can be determined visually or instrumentally, and correlated with the amount of antigen or antibody which was present in the sample.

Such assay techniques, and the use of the solid phase bead or other types of supports for conducting the immunological reactions and changes necessary in such assays, are well known, but have not been without drawbacks. For example, the necessity of elaborate apparatus for conducting the assay and for containing the liquid reagents employed often results in substantial labor and equipment costs, especially for low-volume testing of individual samples. Moreover, the accuracy and reproducibility of such assays may often be less than optimum, since it is sometimes difficult to manufacture conventionally-coated solid supports and other apparatus associated with such assays so that, for a particular assay, all of the materials used therein are specifically designed to meet predetermined sensitivity and specificity requirements. Accordingly, a need exists for relatively simple, easy to-use and comparatively inexpensive solid-phase materials and analytical devices which advantageously can be used in EIA procedures, and which are capable of producing rapid, sensitive and highly reproducible results comparable to conventional methodologies such as the aforedescribed, without the necessity for numerous, cumbersome wet chemical steps or complex instrumentation.

SUMMARY OF THE INVENTION

The present invention directly addresses the foregoing need, and provides, in one aspect, a novel device useful in the performance of a binding assay to determine the presence or amount of an analyte in a test sample, and an assay utilizing the device. In another aspect, the present invention provides an improved, solid phase analytical device, and a binding assay using the device, which is highly advantageous over devices and assay methods of the prior art. In yet another aspect, the present invention provides unique, on-board procedural controls for use with solid phase analytical devices.

An improved device of the invention comprises a reaction site for performing a binding assay. In one aspect, a flow through assay device has a first sample contacting surface and a second surface opposed to the first surface. The substantially planar layer is disposed in the device such that, when the device is used in the performance of a binding assay, at least a portion of the sample contacting the first surface passes through the substantially planar layer to the second surface. Preferably, the assay device of the invention additionally comprises filtering means disposed in relationship to the first surface of the substantially planar layer, such that, when the device is in use, sample fluid passes through the filtering means prior to contacting the first surface. It is further preferred that the device of the invention comprise absorbent means (for absorbing fluid passing through the substantially planar layer).

The concepts of the invention are advantageous not only in the performance of binding assays to determine the unknown presence or concentration of various analytes in test samples, but also to provide on-board controls for solid phase assay devices. As described in more detail, infra, the preferred solid-phase analytical devices in accordance with the invention incorporate assay controls, such as a visible positive control area for displaying a negative result which enables unambiguous interpretation of test results in a visual assay system. Also, for example, a preferred procedural control device utilizing the concepts of the invention can comprise the material of the invention, the material having within its porous matrix of fibers a substance capable of producing a detectable response to an analyte in a test sample under analysis.

According to the present invention improved methods for performing a binding assay, utilizing the material and device of the invention, are provided. In one such preferred method, a sample containing an analyte, e.g., antigen or antibody, is contacted with a reaction surface made from the a porous material which can comprise solid particles returned and immobilized on the material. The method of contacting the reaction site can be by any of a number of means, preferably, by singly applied drops where the reaction site is located on a porous material in a flow-through device or by chromatographic flow where the reaction site is located on a chromatographic strip. The analyte becomes bound to the reagent upon the particles retained within the material the reaction surface is then contacted with a second "labeled" reagent also capable of becoming bound to the analyte which is bound by the reagent retained within the material. Alternatively, the second reagent can be an unlabeled antibody, followed then by addition of labeled substance or reagent directed against the antibody (Amplification or Indirect immunoassay). Thereafter, unbound material is removed, e.g., by washing, and the device is contacted with an indicator substance which, in the presence of the "label" of the second reagent, produces a detectable response which is indicative of the presence and/or amount of the analyte in the sample. Such a detectable response can be read visually or instrumentally, and can advantageously be a color response, most desirably in the form of the visible appearance of a "+" or "−" sign to indicate the result of the assay, particularly if only positive or negative results, respectively, from the assay are necessary or desired. Alternatively, quantitative or semi-quantitative results can be obtained by visually or instrumentally reading the detectable response.

DETAILED DESCRIPTION OF THE INVENTION

The novel readable responses of the present invention, and devices produced therefrom, although applicable to many types of analysis, are especially advantageous when used in immunoassays, to improve conventional solid-phase immunoassay techniques for performing colorimetric or other EIA of biological fluids, such as previously described. Moreover, devices produced in accordance with the invention are relatively easy to use, and require fewer procedural steps and less complex assay technique, by comparison with prior art assays, and also provide the additional advantage of rapid quantitative, semi-quantitative or qualitative results for testing of unknown samples. The material and devices are additionally adapted for advantageous use as controls, e.g., to assess the accuracy and reliability of such assays. Moreover, during manufacture, devices of the invention can be relatively easily made. Assays utilizing such devices of the invention have also been found to be highly sensitive to various levels of analytes. The foregoing advantages, as well as other advantages, will be apparent from the detailed description of the invention as set forth herein.

The concepts of the present invention are applicable to various types of binding assays. Schematic representations of examples of several such types of assays for antigen and antibody analytes can be set forth as follows. However, it will be appreciated that one skilled in the art can conceive of many other types of assays, including analytes other than antigens or antibodies, to which the present inventive concepts can be applied.

1. Direct Assays

A. Antigen (Ag) Assay

| | Solid Phase | Analyte | Labelled anti-analyte |
|---|---|---|---|
| microparticle | )—( Ab | ◇ Ag | )— label Ab$_2$ |

Ab, may or may not be the same as Ab$_2$ and may consist of a variety of monoclonal antibodies or polyclonal antibodies.

Examples of antigen analytes determinable according to the invention using the foregoing reaction scheme include, without limitation, Strep A, beta hCG and hepatitis B surface antigen (HBsAg).

B. Antibody (Ab) Assay

| (i) | Solid Phase | Analyte | Labelled anti-analyte |
|---|---|---|---|
| microparticle | )O Ag | )— Ab | )— label |

Analyte examples (not limitative):
a—HTLV—III;
a—HBc—IgM;
a—Rubella

| (ii) | Solid Phase | Analyte | Labelled Anti-analyte |
|---|---|---|---|
| microparticle | )—(◇ Ab Ag | )— Ab | )— label |

2. Indirect Assays

| | Solid Phase | Analyte | Ab$_1$ | Labelled anti-Ab$_1$ |
|---|---|---|---|---|
| microparticle | )—( Ab | ◇ Ag | )— Ab | )— label Ab |

This is a group of assays where the label is not directed against the analyte. In this embodiment, anti-Ab, may be directed against Ab, in general, or may be directed against one or more functional groups incorporated into Ab.

It is also desirable, in some cases, to capture the analyte directly on the solid phase, as follows:

| | Solid Phase | Analyte | Ab | Labelled anti-Ab |
|---|---|---|---|---|
| microparticle | ) | ◇ Ag | )— Ab | )— label Ab |

3. Competitive Assays

| | Solid Phase | | |
|---|---|---|---|
| | | Sample: | )— |
| microparticle | )O Ag | Label: | )— label |

In assay scheme 3, both the sample and the label are directed against the antigen on the solid phase. The amount of label bound reflects the amount of antibody in the sample.

Figure 1:
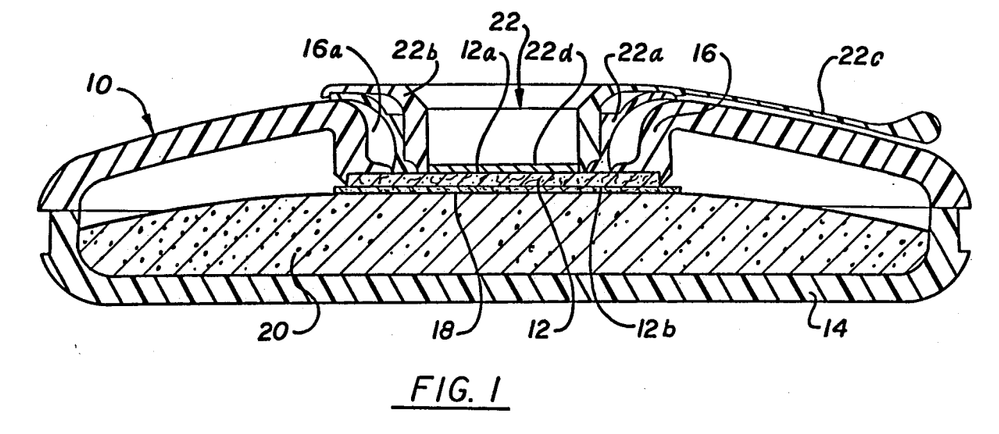
FIG. 1 is a side view in partial cross section of an analytical device in accordance with the present invention.
Figure 2:
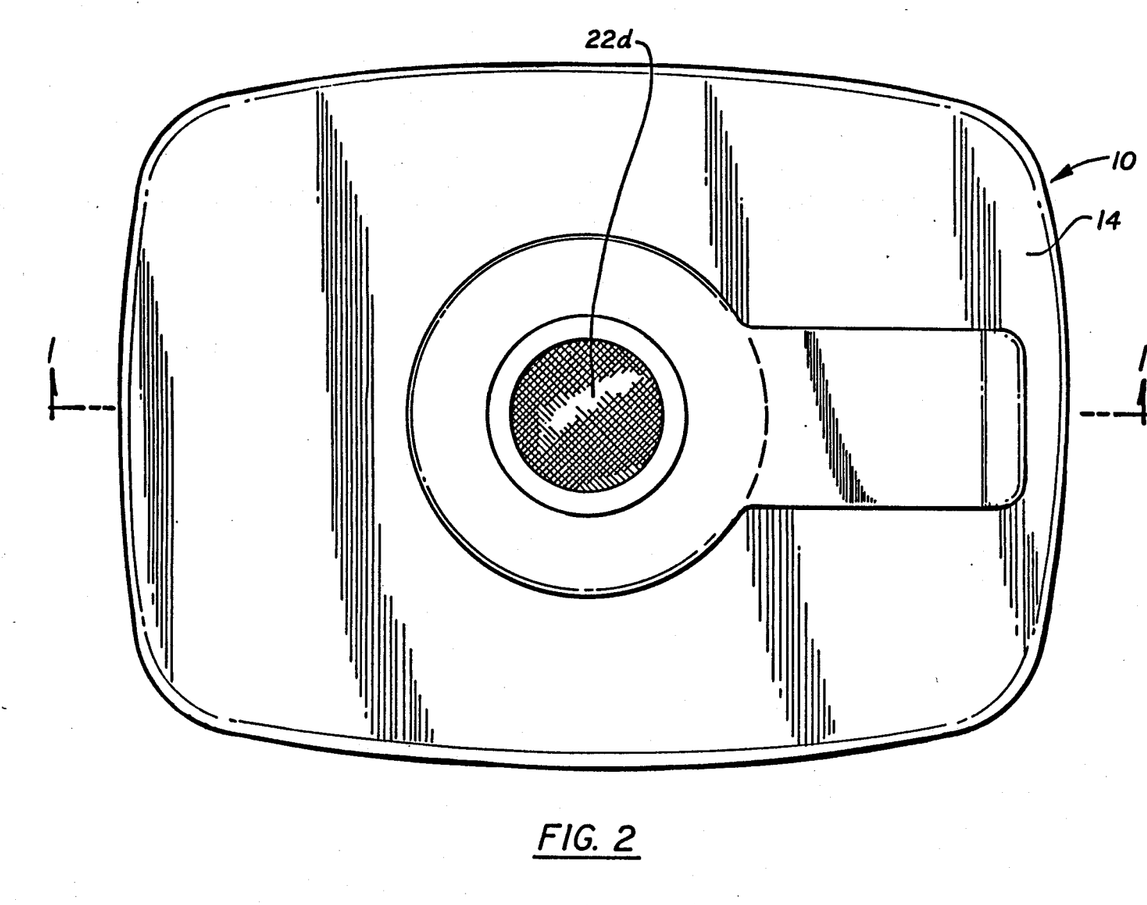
FIG. 2 is a top plan view of the device of FIG. 1.

Referring to FIGS. 1 and 2 of the drawings, an embodiment of an analytical device of the present invention is shown generally at 10 (commercially available from Abbott Laboratories, North Chicago, Ill. under the trademark TESTPACK). The device 10 includes a substantially planar, generally circular, disk-shaped reaction matrix 12. The matrix 12 is disposed within the device 10 such that within the matrix 12 the various chemical reactions and changes necessary to a binding assay can take place when the device 10 is used in the performance of such assays, to determine the presence or amount of analyte(s) in a sample under analysis. The matrix 12 has a sample-contacting surface (reaction site) 12a and a surface 12b opposed therefrom; a preferred composition of the matrix 12 is described in greater detail in the Examples, infra.

Figure 3A:
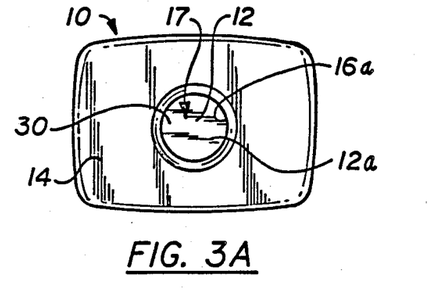
FIGS. 3A, 3B and 3C are top plan views of a particularly preferred embodiment of the device of FIG. 1.

The device 10 additionally includes a carrier 14 within which the matrix 12 is disposed. The carrier 14 can be made of any suitable material such as plastic, metal or other rigid or semi rigid substance. Especially preferred as a material for the carrier 14 is a plastic commercially known as "ABS", and available from the Monsanto Company, St. Louis, Mo. In the preferred embodiment shown, the carrier 14 completely surrounds the matrix 12 and functions as a support and holder therefor. In order to accomplish this function, the carrier 14 has a generally circular flange 16 for supporting and holding tightly the matrix 12. As best shown in FIGS. 1 and 3a, a fluid chamber 17 for receiving a fluid sample and reagents used in the performance of an assay is defined in the device 10 by a sidewall formed by the outer wall surface 16a of the flange 16 and a base wall formed by the sample contacting surface (reaction site) 12a of the matrix 12.

The device 10 further comprises absorbent means 20 disposed in the carrier 14, as shown, for absorbing fluids during use of the assay device. The absorbent means 20 of the device 10 can comprise one or more layers of material and is in physical contact, as shown, with the barrier material 18, when used, or with the reaction matrix 12. This especially advantageous feature enables excess fluid, during the performance of an assay using the device 10, to be easily absorbed, as necessary, after passage of such excess fluid from the reaction matrix 12 during the assay procedure. The absorbent means 20 can be virtually any moisture or fluid retaining material, e.g., that available from James River, and designated "105 point" or "50 point", or, as is especially preferred, a combination of one of more layers of each of the foregoing.

In another aspect of the device 10, barrier means are provided for restricting fluid flow in solid phase analytical devices. This aspect is particularly advantageous when used in solid phase analytical devices having a permeable reaction surface or matrix, or filter layer, and an absorbant layer for absorbing fluids used in the device to permit the flow of fluids from the reaction surface to the absorbant means or layer while preventing the back flow of fluids from the absorbant layer to the reaction matrix.

As shown in FIG. 1, the barrier means comprises a layer of barrier material 18 extending under the matrix 12 and within the carrier 14. The barrier material 18 is in contact with the surface 12b of the matrix 12, and functions, when the device is in use, to restrict fluid passing through the matrix 12, to and through the surface 12b, and into the layer 18, from re contacting the surface 12b. It is to be appreciated that although it is most preferred in a device of the invention to utilize the layer 18 as a fluid restrictive layer, to help to prevent or eliminate "background" interference in the matrix 12, this feature is not essential or critical to the basic functions or concepts of the matrix 12, and usually can be omitted from the device if desired. If omitted, the device generally will perform satisfactorily in an assay, but possibly with less sensitivity (diminished detectable response).

The layer 18 can comprise any suitable material capable of restrictive, substantially "one-way" flow of fluid or moisture. Examples of especially suitable materials for this purpose are polyethylene weave materials manufactured and sold by Ethyl Visqueen Corp., Baton Rouge, La. under the designations "X-6057" (1.0 mil) and "X-6108" (1.25 mil) as well as those materials described in U.S. Pat. Nos. 3,929,135 and 4,342,314.

It is to be appreciated that in addition to the capability of the device 10, as described infra, to produce a visually readable response such as color development indicative of an analyte in a test sample, instrumental determination can be made of a detectable response therefrom, e.g., corresponding to the reflectance of visible light, or intensity of fluorescence or the like, produced by the matrix 12 as a result of the chemical and biological reactions and changes which occur therein when an assay is performed. Accordingly, the detectable response from the device 10 can be measured by, for example, a conventional spectrophotometer. For example, if the detectable response in the matrix 12 produced by the reactions and changes during a particular assay is one wherein a color is developed, and wherein increasing color development indicates an increasing level of a particular analyte in a test sample undergoing analysis, then a diminishing level of light reflected from the matrix 12 to the spectrophotometer corresponds to that increased level of analyte in the sample. The interpretation of such results is capable of being accomplished in ways well known to those skilled in the art, such as by conversion of analog signals generated by the detector of the spectrophotometer to digital information using largely conventional electronics. Such electronics are also well known to those skilled in the art, and are capable of producing a human-readable signal from such digital information which corresponds or correlates to the presence and/or amount of analyte in the test sample.

Figure 5:
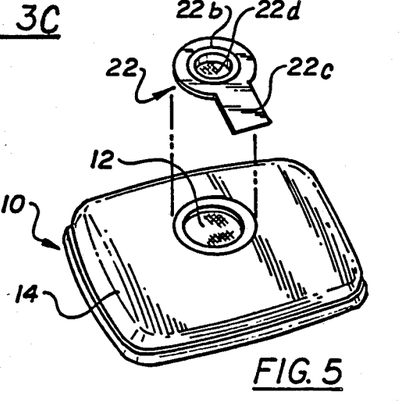
FIG. 5 is a perspective view of the device of FIG. 1, showing the pre-filter removed from the body of the device.

Referring now in more detail to FIGS. 1, 2 and 5 of the drawings, the analytical device 10 of the invention can further include filtering means 22 disposed over reaction site or surface 12a of the reaction matrix 12. The filtering means 22 is press fitted into the carrier 14 by means of a retaining ring 22a, and preferably has a removable portion 22b having a handle portion 22c. The means 22 is further composed, for example, of a suitable porous, fibrous material 22d such as a glass or cellulose filter membrane in a plastic surround; especially preferred are "Lydair TM Grade 254" from Lydall, and "GF/F" or "GF/D" from Whatman, either singly or in combination. When the device 10 is used to perform an assay, the means 22 can perform various functions. Depending upon the type of assay being performed and the nature of the test sample, the means 22 can perform such functions as a reservoir to retain sample or slow the passage of sample or reagents to the reaction matrix 12; as a vehicle to retain reagents, e.g., lyophilized reagents, to be used in an assay; and as a "prefilter" to remove extraneous articulate matter in a sample, or, for example, to separate and to hold blood cells from a whole blood sample while allowing plasma to pass through. In addition, as shown in FIG. 5, if the filter means 22 is at least partially removable from the device 10 (a feature preferred but not essential in the present invention), then during performance of an assay using the device 10, the removable portion 22b of the filter means 22 can be removed, as desired, during a step of the assay in order to remove material which may be retained therein, or to expose the reaction matrix 12 for the addition of reagents or to read a detectable response therefrom. In this case the membrane portion of the filter means 22 is an integral part of the removable portion thereof 22b.

In accordance with the invention, the material useful in the analytical device and methods of the invention comprises a porous, fiber matrix. By "porous" is meant that the matrix is composed of a material into which fluids can flow and can easily pass through. In the material of the present invention, the property of porosity can be achieved simply by selection of an appropriate raw material, such as glass, cellulose, plastic nylon or other fibrous material well known to those skilled in the art.

For example, an especially preferred material for use is "Whatman GF/D" glass fiber filter paper, which has a nominal thickness of 0.032 inch. The thickness of such a material is not critical, and will be a matter of choice for the routineer, largely based upon the properties of the sample (and analyte) being assayed, such as its fluidity and the necessity to retain enough of the sample within the material for a long enough time to enable sufficient binding of the analyte.

In addition, the fibrous material preferably has a plurality of substantially spherical, solid particles having an average diameter of from about 0.1 to about 10 microns or more, most preferably from about 0.1 to about 5 microns, retained and immobilized upon the fibers of the material. By "retained and immobilized" is meant that the particles, once upon the fibers of the material, are not capable of substantial movement to positions elsewhere within the material, (i.e., to other fibers), or cannot be removed completely from the material without destruction thereof. The mechanism by which the particles are so retained and immobilized is not known, but may be due to physical surface attractions between the fibers and the particles, and/or between the particles themselves. The particles can be selected by one skilled in the art from any suitable type of particulate material known generally as "microparticles"; such particles are typically composed, e.g., of polystyrene, polymethylacrylate, polypropylene, latex, polytetrafluoroethylene, polyacrylonitrile, polycarbonate or similar materials. Whatever type of microparticles is selected for use in the invention, it is important that the substance or substances of which the particles are composed be capable of holding on the surface of the particles a substance capable of reaction with an analyte in a test sample, e.g., antibody or antigen, or a combination thereof, or be itself capable of holding an analyte on the surface of the particles. Moreover, the size of the particles is not critical, and so long as the average diameter of the particles is substantially within the aforestated range (although it is preferred that the average diameter of the particles be smaller than the average pore size of the fibrous matrix), any type of particles having the foregoing properties is suitable for use.

The material and analytical devices provided by the invention, it is to be appreciated, can be advantageously employed in a wide variety of otherwise well-known assay techniques and procedures, and are not limited in application to the specific immunoassay techniques described in detail herein. They can thus be used in so called "competitive binding" assays or similar binding assay procedures, and in addition, can be employed in other assays such as typical enzyme assays for such analytes as glucose, uric acid or the like, which are not immunoassays but which can advantageously be carried out by initially retaining at least one reagent used in such assays upon the particles within the material or reaction matrix of a device of the invention. It will be readily apparent to those skilled in the analytical arts that the instant invention can be profitably applied to a wide variety of uses in various types of assay procedures, and thus is in no way limited to the specific details of the assays and procedures described herein.

The novel material, and analytical devices, produced in accordance with the principles of the instant invention can, however, be especially advantageously employed in enzyme immunoassays, particularly so called "sandwich" and indirect enzyme immunoassays. Such assays can be performed using the material and devices of the invention in a manner which is substantially more simple than typical "bead" or other assays of the prior art which require relatively elaborate, time consuming and costly equipment and materials. Such assays also have been found to be capable of surprising sensitivity. A generalized example for one presently preferred "sandwich" immunoassay procedure utilizing the material of the instant invention is as follows:

(Step a) Retention of antibody or antigen upon the particles in the material, forming a reaction matrix, as previously described;

(Step b) Application of a test sample containing antigen or antibody to be determined to the matrix;

(Step c) Application of an enzyme conjugated antibody or antigen to the antigen or antibody of (Step b);

(Step d) Washing, to remove unbound material; and (Step e) Application of an indicator substance which, in the presence of the enzyme portion of the conjugate of (Step c), produces a detectable color or other response in the reaction matrix.

A more detailed discussion of how such "sandwich" assay procedures can advantageously be carried out using the device of the present invention is set forth in the Examples, infra.

In accordance with the present invention, a detectable response is produced at the reaction surface or site on a porous material or reaction matrix of an analytical device; the response is one which is indicative of the presence and/or amount of an analyte in a sample under analysis. Such a detectable response, in preferred embodiments of the invention, can be color development following a series of assay steps, such as those previously described, or can be any number of responses well known in the analytical arts and used for similar purposes. For example, the response produced can be one of fluorescence, provided appropriate reagents are employed in the assay, as is well known to those skilled in the art. The response can be also chemiluminescence, or any of a variety of radiative energy responses (e.g., radioactive emissions) detectable either visually, or instrumentally by various known equipment. Thus, it is to be especially appreciated that in use of the materials and devices of the invention, many different types of detectable responses are possible and desirable and the inventive concepts are not limited thereby.

"On board" procedural control areas are provided on solid phase analytical devices to simultaneously display detectable responses corresponding to a positive control (which will display a detectable response indicative of a valid assay result, regardless of the presence or absence of an analyte of interest in a test sample), a negative control (which will display a detectable response change only if the assay results are invalid) and the sample analyte in a single analytical device reaction site. Typical analytical devices for use with the present invention can include flow through assay devices having one or more layers as previously described, a test strip for chromatographic assay devices (e.g., paper) or thin layer chromatographic assay devices (e.g., nitrocellulose) devices in which one or all the reagents are contained in separate zones of a single strip or other porous material in communication therewith.

The same volume of a test sample and assay reagents are simultaneously placed in contact with the procedural controls and test areas, thereby avoiding the necessity of separate control tests as generally practiced in the art. The method of application of sample and reagents to the reaction site can be any manner appropriate for the particular device used. For example, where the device operates as a flow through assay device, sample and reagents can be applied in a drop-wise fashion or otherwise poured onto the procedural control and test areas such that the precise volumes of sample and reagent are contacted to the reaction site. Where the device is a chromatographic assay device or test strip the sample and reagents can be applied to the strip and allowed to flow to and through the reaction site containing the procedural controls and test areas. Regardless of the particular device used, the reaction site containing the procedural controls (negative control and positive control) and analyte binding area is simultaneously contacted by applications of reagent and sample.

It will be apparent to those skilled in the art that the procedural controls or readable results of the invention may be similarly employed with any analytical device having a reaction site capable of simultaneously displaying a plurality or multiplicity of reaction results. Such other types of reaction surfaces include, for example, coated or uncoated fiber matrices, filters, paper or membranes, relatively planar solid surfaces and the like.

Referring now to Figures 3A–C, 4A–C, 6A–C and 7A–C, on-board negative and positive control areas 30 and 32, respectively, are preferably provided at the reaction site on the reaction surface or matrix 12 of the analytical devices 10 or 11. Device 10 is a flow-through device as depicted in FIG. 1 and device 11 is a chromatographic strip. The negative and positive control areas may function in a quantitative manner thereby functioning as negative and positive assay reference controls, or may function in a qualitative manner thereby functioning as procedural controls indicating the validity of procedures and reagents used in the performance of an assay. As used herein, the term "control" includes both quantitative and qualitative embodiments. Negative control area 30 is formed by maintaining the control area 30 of the matrix 12 free of substances which will retain the enzyme label or other signal response material during the normal use of the devices 10 or 11 in the performance of a binding assay, as described herein.

Positive control area 32 is formed by providing a substance capable of binding the enzyme label or other signal response material within the control area 32 of the matrix, regardless of the presence or absence of the analyte of interest in a test sample. As used in connection with the particularly preferred reaction matrix as previously described, positive control area 32 may be formed by coating the microparticles within the control area 32 with the analyte, or other substances capable of binding or retaining the enzyme label within the area 32 during performance of a binding assay. In addition, one or more analyte binding area(s) 34 are provided on the matrix 12 for binding or retaining the analyte of interest from a test sample on the area 34 during the performance of a binding assay. The analyte binding area(s) 34 may be formed in the particularly preferred reaction matrix material described herein by coating the microparticles within the area(s) 34 of the matrix 12 with a substance, such as antigen or antibody, capable of binding the analyte.

Figure 3B:
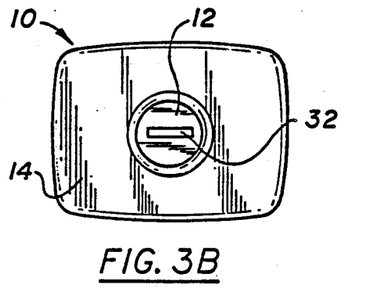
Figure 3C:
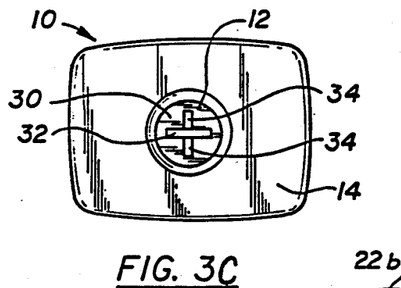
Figures 6A, 6B:
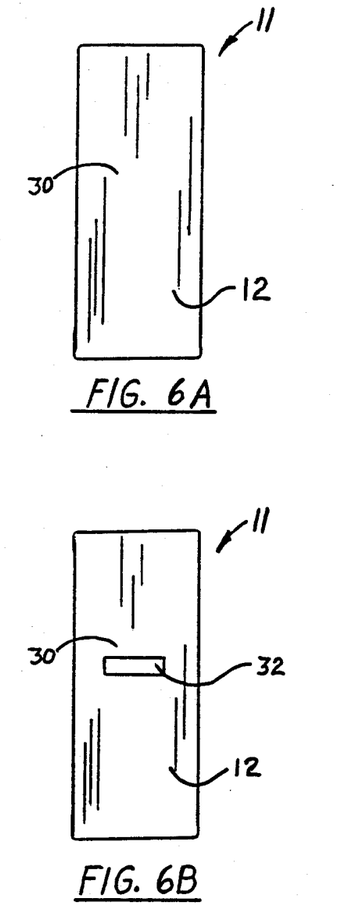
FIGS. 6A, 6B and 6C are top plan views of a particularly preferred embodiment of a chromatographic device.
Figure 6C:
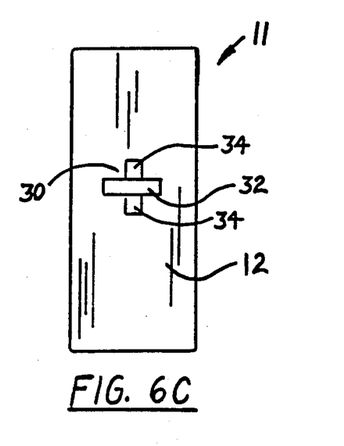

The positive control area 32 and the analyte binding area(s) 34 may be provided in any configuration which facilitates ease of use of the devices 10 or 11 in the performance of a binding assay. However, it is presently preferred to provide the positive control area and the analyte binding area in an interactive configuration in which the positive control area interacts with the analyte binding area upon the occurrence of a positive test result to form a first representational symbol having a known meaning to the user, and the positive control area acts alone upon the occurrence of a negative test result to form a second representational symbol having a known meaning to the user different from that of the first representation symbol. Interactive positive control and analyte binding areas are best shown in the particularly preferred embodiment of FIGS. 3A-C and 6A-C, wherein the positive control area 32 is formed in the shape of a rectangular bar or "−" sign, while the analyte binding areas 34 are formed in the shape of rectangular bars on opposite sides of, and oriented perpendicularly with respect to, the positive control area 32. Accordingly, in use of the devices of FIGS. 3A-C and 6A-C, a positive test result obtained from the proper use of the device 10 will result in a detectable response, in the shape of a "+" sign, in both the positive control area 32 and the analyte binding areas 34, as shown in FIGS. 3C and 6C, indicating a "+" or positive test result to the user. A negative test result obtained from the proper use of the devices will result in a detectable response, in the shape of a "−" sign, in only the positive control area 32, as shown in FIGS. 3B and 6B, indicating a "−" or negative test result to the user. If the binding assay is improperly conducted, or if reagents used in the assay function improperly, no detectable response is obtained in either the positive control area 32 or the analyte binding areas 34, as shown in FIGS. 3A and 6A, indicating an invalid test result. In addition, any detectable response in the negative control area 30, such as may be caused by non specific binding or failure to properly perform washing steps in the performance of the assay, may be indicative of an invalid test result. The configuration of FIGS. 3A-C and 6A-C are presently particularly preferred since it provides immediate information to the user in unambiguous, symbolic form as to the positive (+) or negative (−) nature of the test result, and as to the validity of the assay.

Figure 4A:
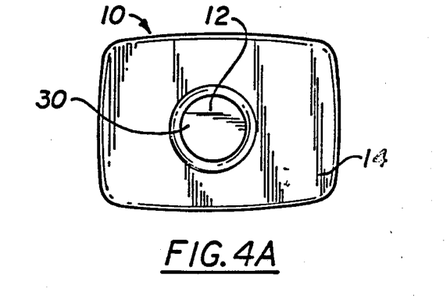
FIG. 4A, 4B and 4C are top plan views of an alternate embodiment of the device of FIG. 1.
Figure 4B:
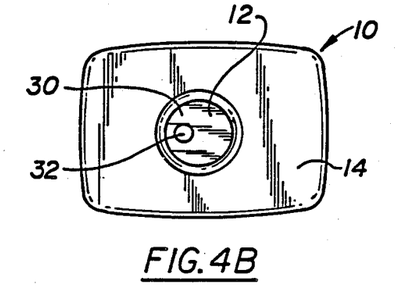
Figure 4C:
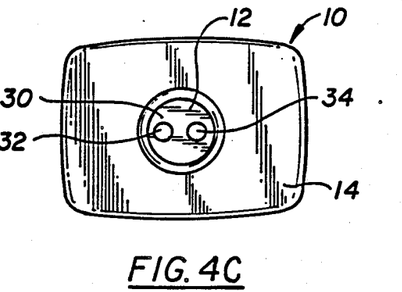
Figures 7A, 7B:
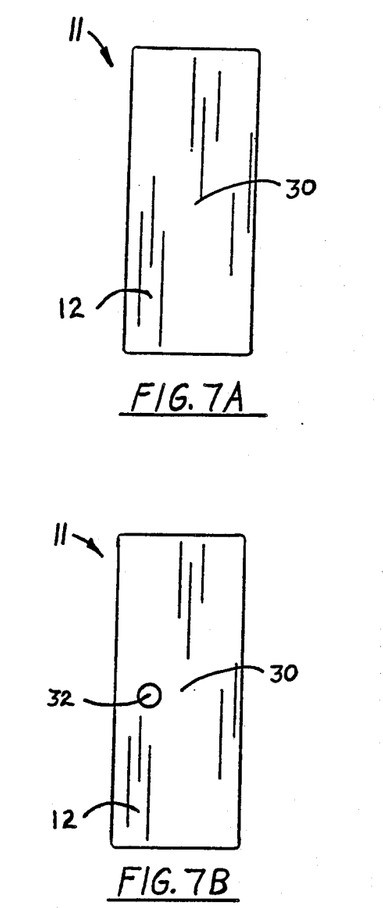
FIG. 7A, 7B and 7C are top plan views of an alternate embodiment of a chromatographic device.
Figure 7C:
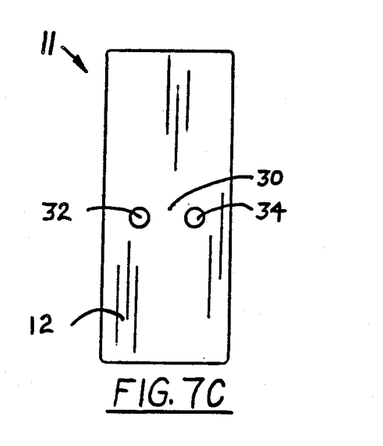

Alternatively, the procedural control areas and the analyte binding areas may be provided in other configurations, as desired. In the alternate embodiments of FIGS. 4A-C and 7A-C, the positive control area 32 and the analyte binding area 34 are formed in the shape of dots, as shown. Thus, a positive test result is indicated by the presence of two dot-shaped detectable response areas, as shown in FIGS. 4C and 7C, a negative test result is indicated by the presence of a detectable response only in the positive control area 32, as shown in FIGS. 4B and 7B, and invalid test result is indicated by the lack of a detectable response as shown in FIGS. 4A and 7A. Other equivalent configurations for the negative control area 30, the positive control area 32 and the analyte binding area(s) 34, such as other symbols, numbers and the like, will be readily apparent to those skilled in the art.

EXAMPLES

The following Examples illustrate preferred ways of making and using the novel material of the present invention, and analytical devices using the material, as well as assay procedures utilizing them. The analytical devices made had substantially the overall shape and appearance of the device shown and described herein with reference to FIGS. 1 and 2 and were prepared and utilized in assays according to the invention using the following procedures. However, the Examples are intended to be only illustrative, and in no way to be construed as placing limitations upon the scope of the invention, which scope is defined solely by the appended claims.

Unless otherwise indicated, all percentages expressed herein are by weight.

EXAMPLE 1: Preparation of Antibody-Coated Microparticles 100 microliters of carboxylate-modified microparticles (2.5% solids; 0.45 microns average diameter; commercially available from Polyscience and Seragen) were added to 1.0 milliliters (ml) of methyl ethyl sulfonate (MES) buffer (5 millimolar (mM), pH 4.75) and 75 microliters of antibody solution (beta-hCG) (2 milligrams per milliliter (mg/ml)). The solution was stirred and then 100 ml of 1-Ethyl 3(3 Dimethyl aminopropyl) carbodimide HCl (EDAC) (2 mg per 10 ml $H_2O$) were added. The solution was stirred overnight at 2-8 degrees C., after which the microparticles were isolated by centrifugation, washed twice with 0.1% "Tween 20" solution, and resuspended in "PBS" Phosphate Buffered Saline (0.01 M KH ; 0.15MNaCl: pH 7.2) to yield a 0.125% solution. After resuspension in PBS, the particles were stored at 2-8 degrees C., for subsequent use in the following procedures.

EXAMPLE 2: Preparation of Solid-Phase Reaction Matrix 50 microliters of the antibody coated microparticles from Example 1 were added dropwise to the center of a Whatman GF/D glass filter; 100 microliters of pig sera were then added and the filter and microparticles incubated for 30 minutes in a humidity chamber at room temperature. After this time, the filter, now containing the microparticles, was washed three times in 300 microliters of PBS buffer. The filter was then stored in a humidity chamber until it was used in the following immunoassay example. The microparticles were observed, by scanning electron microscopy, to have been irreversibly trapped or agglomerated on the glass fibers of the filter material.

It is to be noted that, in addition to the techniques described in the foregoing Example, antibody (or antigen) may be attached to the particles by a variety of methods; e.g., adsorption or use of various chemical activators. Also, it is to be appreciated that the particles can be added to the fibrous matrix after, for example, animal sera has been added, and that the use of such sera is not of critical importance. Therefore, the order of addition of the particles to the matrix and treatment thereof after or before incorporation into the matrix is not critical to the present invention. Moreover, it will be appreciated that coated fibrous materials, such as polystyrene-coated glass, can be used in place of the glass filter matrix material specifically described herein, and the advantages of the invention can also be realized thereby.

EXAMPLE 3: Immunoassay Protocol (Determination of beta-hCG)

The glass fiber material, containing the antibody-coated microparticles as previously described, was cut into substantially circular "disks", and the disks, forming reaction matrices, placed in contact with a blotter material in order to absorb excess fluid from solutions used in the assay. Thereafter, five drops of test samples of human urine (about 280 microliters), containing zero, and 50 and 100 mIU/ml levels of beta-hCG (Table 1, infra), were added to each matrix after passage of the sample drops through a prefilter situated above each matrix. Three drops of an antibody-enzyme conjugate (Table 1, infra) were then added to each matrix through the prefilter, and each matrix was incubated at room temperature for about two minutes. The prefilter was next removed, and 1.0 ml of a detergent wash solution was added to each matrix to remove any excess antibody-enzyme conjugate. Then, one drop of a chromogen indicator (Table 1, infra) was added to each matrix, and after two minutes each matrix was checked visually for color development. Color development was observed for the test samples which contained beta hCG, and the absorbance of light correlating to the color development was determined instrumentally using a conventional spectrophotometer. The results are set forth in the following table.

TABLE 1

| Data for beta-hCG: | Horseradish Peroxidase (HRPO) antibody-enzyme conjugate/3,3',5,5',- tetramethyl benzidine (TMB) chromogen (Absorbance after two minutes at 650 nanometers (nm)) | |
|---|---|---|
| (hCG) mIU/ml in urine samples | Instrumental | Visual |
| 0 | 0.0159 | Not visible |
| 50 | 0.0852 | Visible |
| 100 | 0.2617 | Visible |

TABLE 2

| Data for beta-hCG: | Alkaline Phosphatase antibody-enzyme conjugate/Bromo-chloro indole phosphate nitro-blue tetrazolium chromogen. (Absorbance after two minutes at 650 nanometers) | |
|---|---|---|
| (hCG) mIU/ml in urine samples | Instrumental | Visual |
| 0 | 0.0057 | Not visible |
| 50 | 0.0872 | Visible |
| 100 | 0.1584 | Visible |

The foregoing antibody enzyme conjugates were prepared generally in accordance with the following references: *HRPO:* Nakane, P.K. and Kawaoi, A., *The Journal of Histochemistry and Cytochemistry,* 22 (12) 1084–1091 (1974); *Alkaline Phosphatase:* Prepared by slight modifications to a Glutaric dialdehyde procedure, available from Boehringer Mannheim GmbH.

Urine samples from twelve non pregnant and six confirmed pregnant women were tested using the HRPO-antibody enzyme conjugate, described supra, and substantially the procedure described in Example 3. Twelve samples from the non-pregnant individuals produced no visible color in the reaction matrix; i.e., all absorbences were less than 0.050, below which threshold no color can easily be visualized. Samples from all of the six pregnant individuals produced visible color upon testing.

EXAMPLE 4: Preparation of beta-hCG Procedural Control 1.0 mL of microparticles (as previously described, 0.125% solids), having antibody to beta-hCG attached to their surfaces, were reacted with 14.0 microliters of beta hCG solution (1.0 mg/ml). The solution was stirred for three hours at room temperature, and then stored at 2-8 degrees C. until needed. No further washing of the particles was required.

50 ml of the foregoing procedural control microparticles, having beta hCG bound to their surfaces, were diluted to various concentrations and applied to the glass fiber filter material previously described, in the same manner as the antibody coated microparticles had been applied (described supra). The activity of each dilution was then checked by adding two drops (about 100 microliters) of HRPO-antibody enzyme conjugate, incubating for five minutes, washing with 1.0 ml of a detergent wash solution and then developing color by the addition of one drop (about 50 microliters) of TMB solution. The absorbance of each control was then measured using a conventional spectrophotometer, as set forth in the following table.

TABLE 3

| Dilution of Stock Solution | Absorbance After Two Minutes at 650 nm |
|---|---|
| 1:8 | 0.7118 |

TABLE 3-continued

| Dilution of Stock Solution | Absorbance After Two Minutes at 650 nm |
|---|---|
| 1:32 | 0.2358 |
| 1:64 | 0.0983 |

The absorbance of the procedural control at a 1:32 dilution was found to be approximately equal to that of a 100 mIU/ml beta hCG standard.

EXAMPLE 5: Bacteriological Testing Heterologous Bacteria

Assays for Strep A antigen, and assays for antigens for the various organisms listed in the following table, were performed using devices of the invention as previously described. The protocol of the assays can be summarized as follows:

1. A pre prepared bacterial swab sample (prepared by a well-known technique) was placed into solution and pipetted onto the filter assembly over the reaction matrix of the device. The sample was allowed to pass through the filter.
2. Two drops (about 100 microliters) of antibody-enzyme conjugate were added, and allowed to pass through the filter.
3. The filter was then removed and the matrix washed with 10-12 drops (about 500 microliters) of PBS Buffer.
4. One drop (about 50 microliters) of TMB were added, and color development in the matrix read after about 2 minutes incubation at room temperature.

The absorbance of 650 nanometer light reflected from the matrix was then determined, using conventional reflectance apparatus, as a result of assays performed as aforedescribed on samples which contained the microorganism antigens listed in the following table.

TABLE 4

Assays for Heterologous Bacteria

| Microorganism[a] | Absorbance[b] |
|---|---|
| Serratia marcescens | 0.040 |
| Klebsiella pneumoniae | 0.032 |
| Pseudomonas aeruginosa | 0.045 |
| Neisseria meningitidis | 0.034 |
| Neisseria sicca | 0.036 |
| Haemopnilus influenzae | 0.051 |
| Staphylococcus aureus Cowan I | 0.084 |
| Staphylococcus aureus Cowan II | 0.049 |
| Bordetella pertussis | 0.041 |
| Candida albicans | 0.032 |
| Streptococcus pneumoniae | 0.056 |
| Streptococcus agalactiae (Group B) | 0.054 |
| Streptococcus equisimilis (Group C) | 0.063 |
| Streptococcus faecalis (Group D) | 0.047 |
| Streptococcus cariis (Group G) | 0.101 |
| Streptococcus pyogenes (Group A) | 1.392 |
| Negative Control | 0.049 |

[a]Microorganisms were assayed at a concentration of 10[6] CFU per test.
[b]Absorbance at 650 nanometers.

EXAMPLE 6: Solid Phase Evaluation; Use of Various Reaction Matrix Materials According to the Invention Zero concentration and 250 mIU/ml concentration beta-hCG-containing urine samples were assayed as previously described (Example 3) using microparticles which had been incorporated in various fibrous matrix materials, according to the invention. The materials listed in the following table were of different pore sizes and flow rates. The Whatman GF/D material was also pretreated before addition of the particles. An HRPO conjugate was used. In each assay, color development, indicating success of the assay, was visually observed, and absorbance readings were taken at 650 nanometers. The results are compiled in the following table.

TABLE 5

| Matrix | 0 mIU/ml | 250 mIU/ml | *Pore Size | **Flow-rate |
|---|---|---|---|---|
| 1. Whatman GF/D | .0038 | 0.2284 | 2.7 | 41 |
| 2. Whatman GF/D precoated with polystyrene (4.4 mg/ml THM) | .0057 | 0.2603 | 2.7 | 41 |
| 3. Whatman GF/D precoated with pig sera | .0058 | 0.3883 | 2.7 | 41 |
| 4. Whatman 934-AH | .0041 | 0.2801 | 1.5 | 47 |
| 5. Whatman GF/C | .0008 | 0.1855 | 1.2 | 100 |
| 6. Whatman GF/A | .0059 | 0.1674 | 1.6 | 62 |
| 7. S+S#30 Glass*** | .0036 | 0.3331 | — | — |

*Microns
**Seconds/100 ml at 10 cm head.
***Schleicher and Schnell

The foregoing data indicates that a variety of raw fibrous materials can be used in the novel material and reaction matrices of devices of this invention. Such alternative raw materials can be used after pretreatment with protein sera or polystyrene (hydrophilic or hydrophobic) in order to change somewhat the characteristics of the material, as desired (e.g., flow rate).

EXAMPLE 7: Effect of Particle Size

Particles ranging in size from 0.19 to about 3.0 microns (average diameter) were added to samples of matrix materials (Whatman GF/D)). The amount of antibody per sample was maintained at about 3.0 micrograms, and zero and 100 mIU/ml beta-hCG-containing urine samples were assayed as previously described, using an alkaline phosphatase conjugate. Absorbance readings were taken at 650 nanometers. The results are set forth in Table 6.

TABLE 6

| Average Diameter of Particles (microns) | Zero beta-hCG | 100 mIU/ml beta-hCG |
|---|---|---|
| 0.19 | .0065 | .1037 |
| 0.50 | .0050 | .1500 |
| 0.90 | .0076 | .0825 |
| 3.0 | .0061 | .1227 |

The above results demonstrate that particles ranging in size from 0.19 to about 3.0 microns in diameter are particularly effective, and thus preferred. Particles within the range of from about 0.1 to about 5 microns, however, are suitable for use in the invention. Also, since the pore size of the GF/D filter material is about 2.7 microns, the data shows that particles much smaller, or larger, than the average pore size of the fibrous matrix material can be used.

EXAMPLE 8: Rapid Assay for beta hCG

An advantageously rapid, and procedurally simple assay for beta hCG was conducted using an analytical device which had been produced in accordance with the present invention, as previously shown and described with reference to FIGS. 1 and 2. The assay protocol was as follows.

Five drops of a patient urine specimen were applied from a medicine dropper to the center of a filter over the reaction matrix of the device, using a transfer pipette. The specimen was allowed to soak through the matrix (approximately 10 seconds). Three drops of antibody-enzyme conjugate (alkaline phosphatase) were then added and the reaction matrix incubated for 60 seconds at room temperature.

The filter was next removed and discarded, and about 1 ml of a citrate/NaCl wash solution, combined with Tween and Triton buffer solutions, was added and allowed to flow through the matrix.

Three drops of a chromogenic enzyme substrate (Bromo chloro indole phosphate nitro-blue tetrazolium) were then added, and the color allowed to develop in the matrix for a full two minutes. Thereafter, another 1.0 ml of the wash solution was added, and the results read visually. The appearance of a visually detectable positive sign (+) indicated that the specimen contained elevated (greater than about 50 mIU/ml) levels of beta hCG. Samples run using the foregoing procedure but not containing such elevated levels of beta hCG produced a negative sign (−) in the matrix.

Tests run utilizing a substantially similar protocol to that of Example 8 but which did not result in the appearance of either a positive (+) or a negative (−) sign, indicated the improper addition of reagents, or indicated deterioration of reagents.

The following is a general example of the preparation of an analytical device according to the invention, which additionally incorporates a procedural control area for determining non-specific reactivity (interference) of the sample with the solid phase.

Reaction matrices utilizing the material of the invention can be prepared substantially as previously described, and the particles incorporated into the material in a pattern having substantially the overall shape of a "cross". The vertical axis of the "cross" can be formed of the particles having an analyte binding substance upon their surfaces, whereas the horizontal axis of the "cross" can be formed of a substance capable of binding the enzyme label (i.e., antibody capable of becoming "conjugated" or attached to the label). Accordingly, when these reaction matrices are used in an assay (such as previously described), e.g., for beta hCG, if no detectable level of analyte is present in the sample only the "procedural control area" of the matrix will produce a detectable response, i.e., the horizontal axis of the "cross" (a "minus" sign) will develop color or another response, indicating a negative result. However, if a detectable level of analyte is present, then the analyte will bind, along with the label, to the particles both in the horizontal and vertical axes, producing a detectable response in both axes (a "plus" sign).

Alternatively, the areas of the matrix in which the responses are produced can take the form of "dots", circles, numbers and the like. Thus, the microparticles can be sprayed or otherwise dispensed into the material of the matrix and incorporated therein, as previously described, in various patterns as desired. While the foregoing controls have been described in this Example as used in connection with the presently preferred matrix material of the invention, the on board controls may be similarly employed in connection with other solid-phase analytical devices, as previously described. The advantages of incorporation of such a procedural control into the material and device heretofore described, as well as into solid phase assay devices using other types of matrix materials, include (a) a control provides a measure of validation of materials for each assay run; (b) a control with each assay run enables comparative interpretation of results, especially when specific patterns, such as "plus" ("+") and "minus" ("−") signs are used; and (c) the incorporation of a control into each assay device provides expedient validation of the assay, allowing the user to be more confident of the assay results.

It is to be appreciated that various modifications and changes can be made in the specific, preferred embodiments of the invention as described in detail herein, without departing from the spirit and scope of the invention, as set forth in the following claims.

What is claimed is:

1. A solid phase assay device for use in a binding assay to determine the presence or amount of an analyte in a fluid sample through the use of a label capable of producing a detectable response, said device comprising a reaction site on a porous matrix having,
   a negative control area,
   a positive control area within said negative control area containing immobilized binding reagent for said label, and
   an analyte binding area within said negative control area containing immobilized binding reagent for analyte in the sample,
   said positive control area being shaped such that, in the presence or absence of analyte in the sample and in the presence of said label, a minus symbol is formed representing a negative result, and
   said analyte binding area being shaped such that, taken together with said minus symbol in the presence of said label and analyte, a plus symbol is formed representing a positive result.

2. The assay device according to claim 1, wherein said porous matrix is a substantially planar layer having a first surface comprising said reaction site, and a second, opposed surface.

3. The solid phase assay device of claim 2, wherein said reaction site is capable of being contacted by singly applied drops of the fluid sample.

4. The solid phase assay device of claim 1 wherein said porous matrix is positioned adjacent an absorbent material.

* * * * *